US008873065B2

(12) United States Patent
Yoshida et al.

(10) Patent No.: US 8,873,065 B2
(45) Date of Patent: Oct. 28, 2014

(54) TOMOGRAPHIC IMAGING APPARATUS AND TOMOGRAPHIC IMAGING METHOD

(75) Inventors: Hirofumi Yoshida, Yokohama (JP); Nobuhito Suehira, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 183 days.

(21) Appl. No.: 13/634,215

(22) PCT Filed: Mar. 24, 2011

(86) PCT No.: PCT/JP2011/058161
§ 371 (c)(1),
(2), (4) Date: Sep. 11, 2012

(87) PCT Pub. No.: WO2011/122685
PCT Pub. Date: Oct. 6, 2011

(65) Prior Publication Data
US 2013/0003076 A1    Jan. 3, 2013

(30) Foreign Application Priority Data

Mar. 31, 2010 (JP) ................................ 2010-082813

(51) Int. Cl.
G01B 9/02    (2006.01)
A61B 3/10    (2006.01)
A61B 3/12    (2006.01)
A61B 5/00    (2006.01)

(52) U.S. Cl.
CPC .............. *A61B 3/1225* (2013.01); *A61B 3/102* (2013.01); *G01B 9/02091* (2013.01); *A61B 5/0066* (2013.01); *G01B 9/02044* (2013.01); *A61B 5/0068* (2013.01)
USPC ........................................................ 356/479

(58) Field of Classification Search
CPC .. A61B 3/1225; A61B 5/0068; A61B 5/0066; A61B 5/0073; A61B 3/00–3/185; G01B 9/02044; G01B 9/0209; G01B 9/02019; G01N 21/4795; G01N 2021/17871
USPC .................................................. 356/450–521
See application file for complete search history.

(56) References Cited

U.S. PATENT DOCUMENTS 6,198,540 B1 * 3/2001 Ueda et al. .................... 356/479
6,769,769 B2 * 8/2004 Podoleanu et al. ........... 351/221

(Continued)

FOREIGN PATENT DOCUMENTS

JP    2008-145187 A    6/2008
JP    2008-145429 A    6/2008
JP    2008-298767 A    12/2008
JP    2010-012166 A    1/2010

*Primary Examiner* — Kara E Geisel
*Assistant Examiner* — Violeta A Prieto
(74) *Attorney, Agent, or Firm* — Canon, U.S.A., Inc. IP Division

(57) ABSTRACT

A tomographic imaging apparatus includes an irradiation unit configured to irradiate with a plurality of measurement light beams, a sensor configured to convert into an electric signal a plurality of combined light beams via an optical imaging system by making return light beams from an inspection target, which are generated due to the plurality of measurement light beams, interfere with reference light beams, an output unit configured to output light beams of a single wavelength based on a wavelength width of the plurality of measurement light beams, and a generation unit configured to generate a tomographic image from an electric signal acquired by the sensor via the imaging optical system, based on a position of the light beam of the single wavelength on the sensor.

7 Claims, 14 Drawing Sheets

(56) References Cited

U.S. PATENT DOCUMENTS

| | | | |
|---|---|---|---|
| 7,061,622 B2 * | 6/2006 | Rollins et al. | 356/497 |
| 7,436,512 B2 * | 10/2008 | Ida et al. | 356/328 |
| 7,570,364 B2 * | 8/2009 | Kuroiwa | 356/479 |
| 7,933,024 B2 * | 4/2011 | Hirose | 356/497 |
| 7,982,881 B2 * | 7/2011 | Fercher et al. | 356/497 |
| 8,204,300 B2 * | 6/2012 | Sugita et al. | 382/154 |
| 8,425,036 B2 * | 4/2013 | Yoshida et al. | 351/205 |
| 8,634,081 B2 * | 1/2014 | Suehira et al. | 356/479 |
| 8,678,588 B2 * | 3/2014 | Makihira et al. | 351/206 |
| 2008/0284981 A1 | 11/2008 | Fercher | |
| 2008/0285043 A1 * | 11/2008 | Fercher et al. | 356/451 |
| 2010/0007894 A1 * | 1/2010 | Suehira | 356/497 |
| 2011/0176142 A1 * | 7/2011 | Hacker et al. | 356/479 |
| 2011/0242487 A1 * | 10/2011 | Yuasa et al. | 351/206 |
| 2011/0273668 A1 * | 11/2011 | Hirose | 351/206 |
| 2011/0299035 A1 * | 12/2011 | Suehira | 351/206 |
| 2012/0002214 A1 * | 1/2012 | Utsunomiya et al. | 356/498 |
| 2012/0062901 A1 * | 3/2012 | Yoshida et al. | 356/479 |
| 2012/0257165 A1 * | 10/2012 | Suehira | 351/206 |
| 2013/0003076 A1 * | 1/2013 | Yoshida et al. | 356/479 |
| 2013/0003077 A1 * | 1/2013 | Suehira et al. | 356/479 |

* cited by examiner

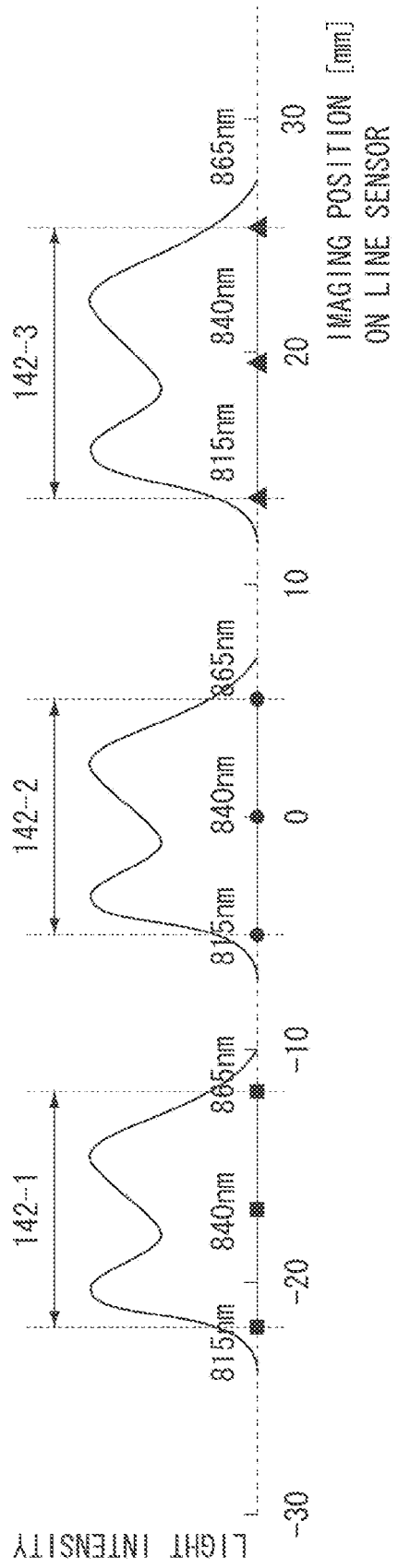

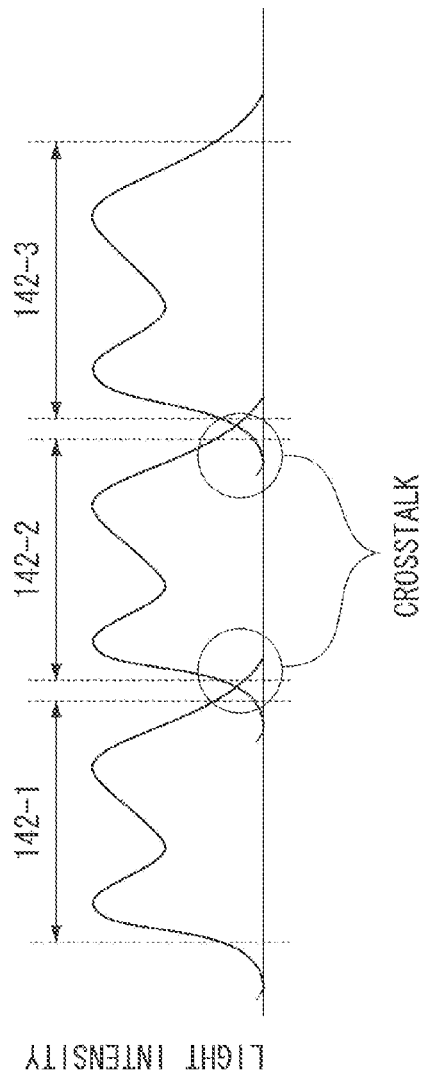

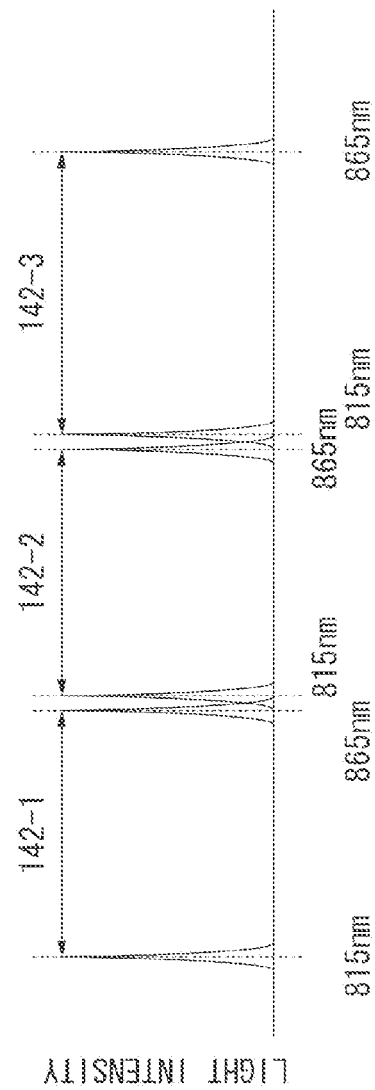

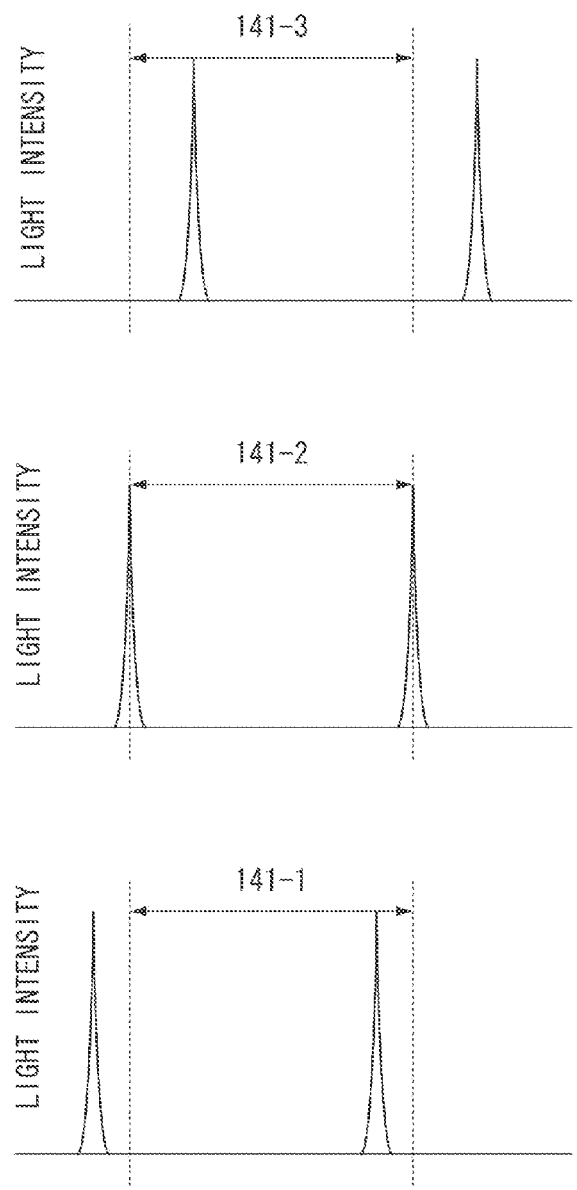

TOMOGRAPHIC IMAGING APPARATUS AND TOMOGRAPHIC IMAGING METHOD

TECHNICAL FIELD

The present invention relates to a tomographic imaging apparatus and, more particularly, to a technique for finding relation between an imaging position of interference light and a position of a tomographic image.

BACKGROUND ART

Currently, various apparatuses using optical devices are used as ophthalmologic apparatuses. For example, an anterior ocular segment photographing apparatus, a fundus camera, and a confocal scanning laser ophthalmoscope (SLO) are used as optical devices for observing eyes. Thereamong, a tomographic imaging apparatus based on optical coherence tomography (hereinafter referred to as "OCT") utilizing multiwavelength lightwave interference is an apparatus capable of obtaining a tomographic image of a sample at high resolution. The tomographic imaging apparatus is becoming indispensable for retina-specialized outpatient departments as ophthalmologic apparatuses.

The tomographic imaging apparatus splits low-coherence light from a light source into reference light and measurement light. Then, the tomographic imaging apparatus irradiates an inspection target with the measurement light and causes the reference light to interfere with return light from the inspection target. Thus, the tomographic imaging apparatus can measure a tomographic layer of the inspection target. The tomographic imaging apparatus can obtain a high-resolution tomographic image (hereinafter sometimes referred to as an "OCT tomographic image") by scanning a sample with measurement light. Accordingly, tomographic images of a retina of a fundus of a subject's eye are acquired. Such tomographic images are widely used for ophthalmologic diagnoses. However, if the inspection target is a biological organ such as an eye, in order to suppress distortion of an image due to a motion of an eye, it is required to measure a tomographic layer at high speed with high sensitivity.

The United States Patent Application Publication No. 2008-0284981 discusses, as one of such methods, a method for simultaneously measuring data at a plurality of points on an inspection target. According to this method, light from a single light source is split by a slit so as to form a plurality of light sources. Then, each of light beams from the plurality of light sources is split by a beam splitter into a measurement light beam and a reference light beam. Each measurement light beam is applied onto an inspection target. A return light beam from the inspection target and the reference light beam are combined with each other by the beam splitter. Then, a plurality of combined light beams are incident upon a diffraction grating, and simultaneously detected by a two-dimensional sensor. Thus, the method discussed in the United States Patent Application Publication No. 2008-0284981 enables speed-up of the measurement by simultaneously measuring data using a plurality of measurement light beams.

However, when a single image is generated from images obtained by performing the measurement of data at a plurality of points on an inspection target, each connection part between the obtained images is noticeable according to a configuration of an optical system. More specifically, if interference light beams differ from each other in incidence angle to the diffraction grating, even when the incident light beams having the same wavelength width are incident thereupon, pixel widths detected on a sensor differ from one another due to characteristics of diffraction. Consequently, OCT images generated from the interference light beams differ from one another in contrast depending upon a depth direction of the inspection target, and in resolution.

SUMMARY OF INVENTION

The present invention is directed to a tomographic imaging apparatus and a tomographic imaging method, which suppress variation in image quality depending upon an imaging position of a tomographic image.

According to an aspect of the present invention, a tomographic imaging apparatus for imaging a tomographic image using combined light obtained by causing an interference system to make return light due to irradiation of measurement light onto an inspection target and reference light, interfere with each other, includes an output unit configured to output light of a specific wavelength, a sensing unit configured to sense light of the specific wavelength via the interference system, and a detection unit configured to detect a detection position on the sensing unit, at which the light of the specific wavelength is sensed by the sensing unit.

According to another aspect of the present invention, a tomographic imaging method for imaging a tomographic image using combined light obtained by causing an interference system to make return light due to irradiation of measurement light onto an inspection target and reference light, interfere with each other, includes outputting light of a specific wavelength, sensing light of the specific wavelength via the interference system, and detecting a detection position on the sensing unit, at which the light of the specific wavelength is sensed.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

FIG. 4A conceptually illustrates each spectroscopic position on and each crosstalk occurring in a line sensor in the tomographic imaging apparatus, respectively.

FIG. 4B conceptually illustrates each spectroscopic position on and each crosstalk occurring in a line sensor in the tomographic imaging apparatus, respectively.

FIG. 5B conceptually illustrates outputs of the line sensor in the tomographic imaging apparatus at the time of making single-wavelength light incident thereon.

FIG. 10 illustrates outputs of the line sensor according to the second exemplary embodiment of the present invention.

DESCRIPTION OF EMBODIMENTS

Various exemplary embodiments, features, and aspects of the invention will be described in detail below with reference to the drawings.

Hereinafter, a tomographic imaging apparatus to which the present invention is applied, i.e., a first exemplary embodiment of the invention is described with reference to FIG. 1.

Figure 1:
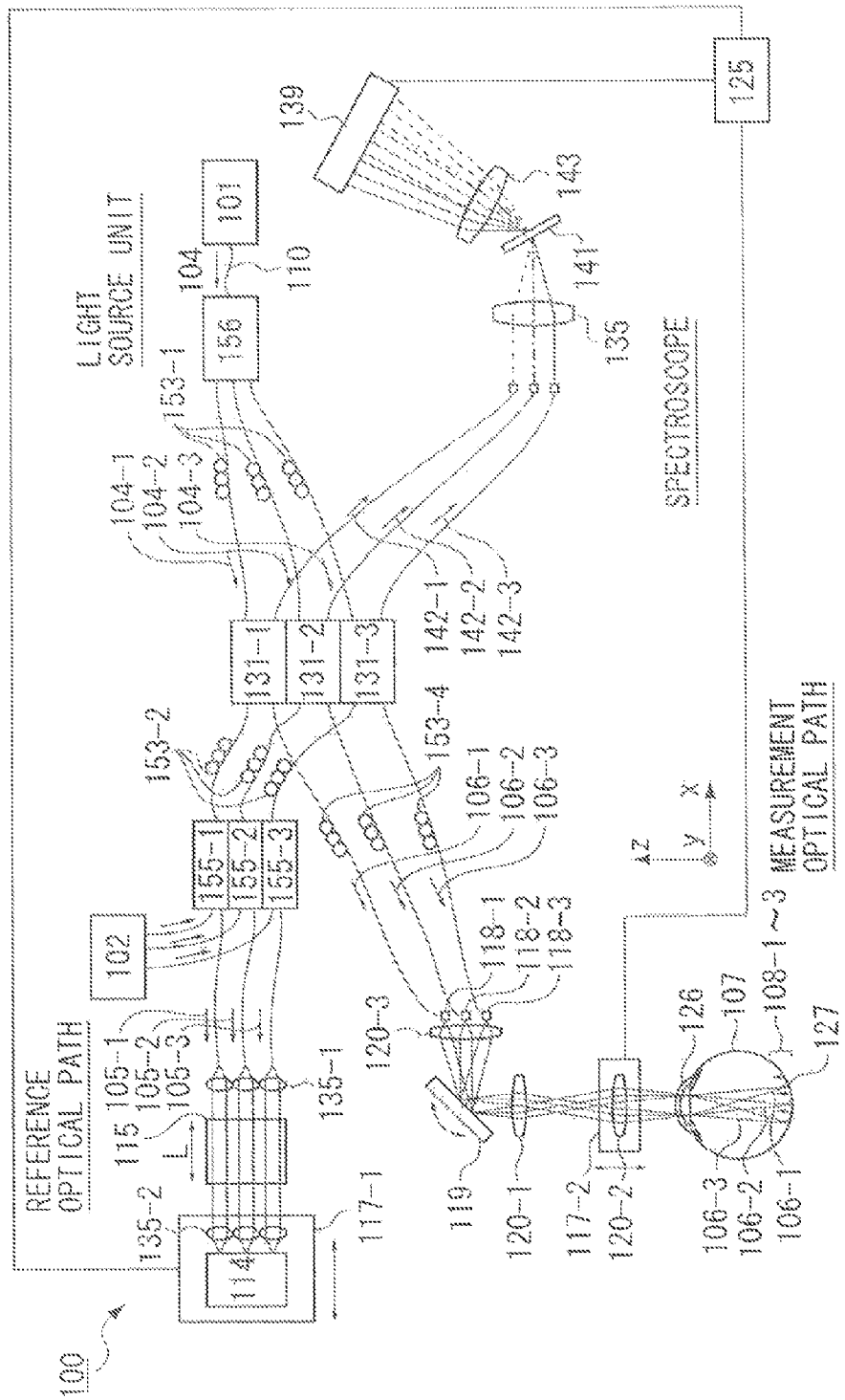
FIG. 1 illustrates a configuration of a tomographic imaging apparatus as an exemplary embodiment of the present invention.

As illustrated in FIG. 1, the entire tomographic imaging apparatus 100 according to the present exemplary embodiment configures a Michelson interferometer. Light output from a broadband light source is split into a plurality of light beams each of which is further split into a measurement light beam and a reference light beam. An inspection target is irradiated with a plurality of measurement light beams through a plurality of measurement light paths so as to become return light beams. The tomographic imaging apparatus 100 includes an OCT system for imaging a tomographic image of an inspection target using a plurality of combined light beams obtained by combining and optically interfering return light beams based on the plurality of measurement light beams, with reference light beams passed through reference light paths, respectively.

Optical System

Each output light beam 104 output from a broadband light source 101 is led by a single mode fiber 110 to an optical coupler 156 to be incident upon an optical coupler 156. The output light beam 104 is split by the optical coupler 156 into output light beams 104-1 through 104-3 respectively passing through three light paths, i.e., first, second, and third light paths. Then, each of the three output light beams 104-1 through 104-3 passes through polarization controllers 153-1 and is split by a corresponding one of optical couplers 131-1 through 131-3 into reference light beams 105-1 through 105-3 and measurement light beams 106-1 through 106-3.

Each of the three split measurement light beams 106-1 through 106-3 is returned as return light beams 108-1 through 108-3 reflected or scattered at measurement places of a retina 127 or the like in a subject's eye 107 to be observed. Then, the return light beams 108-1 through 108-3 are combined with the reference light beams 105-1 through 105-3 passing through the reference light paths by the optical couplers 131-1 through 131-3 so as to become combined light beams 142-1 through 142-3. The combined light beams 142-1 through 142-3 are dispersed by the transmission type diffraction grating 141 into spectra of various wavelengths, which are incident upon a line sensor 139. The line sensor 139 converts, to a voltage, light intensity corresponding to each position (i.e., each wavelength) on the line sensor 139. A personal computer 125 forms a tomographic image of the subject's eye 107 using an electric signal representing the voltage. In the following description of the present exemplary embodiment, an optical system for emitting light onto the line sensor 139 is referred to as an imaging optical system. In an example of the present exemplary embodiment, it is assumed that the imaging optical system includes a lens 135, a transmission type diffraction grating 141, and a lens 143.

Surrounding conditions of the broadband light source 101 are described hereinafter. The broadband light source 101 is a super luminescent diode (SLD) which is a typical low coherence light source. In view of wavelengths suitable for measuring a subject's eye, far-red light is suitable for light output from the light source. Because the wavelength of light from the light source affects a resolution in a lateral direction of an obtained tomographic image, it is desirable that the wavelength of the light is as short as possible. In this example, it is assumed that a central wavelength is 840 nanometers (nm), and that a wavelength width is 50 nm. However, any other wavelength can be selected according to a measurement site of an observation target. Although SLD is selected as the type of the broadband light source, any other type of a broadband light source can be used, as long as the light source can output low coherence light. For example, an amplified spontaneous emission (ASE) type broadband light source can be used as the light source.

Next, a light path for the reference light 105 is described hereinafter. Each of the three reference light beams 105-1 through 105-3, into which light from the light source is split by the optical couplers 131-1 through 131-3, passes through polarization controllers 153-2 and optical couplers 155-1 through 155-3. Then, the reference light beams are output by lenses 135-1 to be substantially parallel light beams. Next, each of the reference light beams 105-1 through 105-3 passes through a dispersion compensation glass 115 and is converged by lenses 135-2 to a mirror 114. Then, the reference light beams 105-1 through 105-3 change direction at the mirror 114 and travel towards the optical couplers 131-1 through 131-3 again.

Next, the reference light beams 105-1 through 105-3 return to the optical couplers 131-1 through 131-3. The dispersion compensation glass 115 compensates the reference light 105 for dispersion corresponding to a time when the measurement light 106 reciprocates between the subject's eye 107 and a scanning optical system. The length L of the dispersion compensation glass is assumed to be a typical value of a diameter of a Japanese average-sized eyeball. Thus, L=23 millimeters (mm). An electric stage 117-1 can move in a direction indicated by an arrow and adjust and control a light path length of the reference light 105.

The electric stage 117-1 is controlled by the personal computer 25. The same mirror 114, the same electric stage 117-1 and the same dispersion compensation glass 115 are used for each of the three reference light paths in the present exemplary embodiment. However, the reference light paths can be configured independent of one another. In this case, positions of the lens 135-2 and the mirror 114 are controlled by different electric stages 117-1 such that the light path length corresponding to each of the reference light beams 105-1 through 105-3 can be changed.

The single-wavelength light source 102 is connected to a distal end of each of light paths branched from the optical couplers 155-1 through 155-3 other than the light paths for the reference light beams 105-1 through 105-3. The single-wavelength light source 102 is configured to output light having a wavelength of 815 nm and light having a wavelength of 865 nm. An exemplary-form of the single-wavelength light source 102 includes, e.g., a broadband light source and an optical filter. The optical filter is configured to transmit or reflect light of a specific wavelength.

Next, a light path for the measurement light 106 is described hereinafter. Each of the measurement light beams 106-1 through 106-3 respectively split by the optical couplers 131-1 through 131-3 passes through a polarization controller 153-4 and is output from fiber ends 118-1 through 118-3. Then, the measurement light beams 106-1 through 106-3 are made by a lens 120-3 to be substantially parallel light beams. The substantially parallel light beams are output therefrom and incident upon a mirror of an XY-scanner 119 configuring the scanning optical system. For simplicity of description, the XY-scanner 119 has been described as having a single mirror. However, the XY-scanner 119 can actually be configured so that two mirrors, i.e., an X-scan mirror and a Y-scan mirror are arranged close to each other, and that raster scanning is performed on the retina 127 in a direction perpendicular to an optical axis thereof. Alternatively, the XY-scanner 119 can actually be configured so that each of the X-scan mirror and the Y-scan mirror is placed so as to be conjugated with a pupil. Lenses 120-1 and 120-2 configure an optical system for scanning the retina 127 with the measurement light beams 106-1 through 106-3. The lenses 120-1 and 120-2 serve to scan the retina 127 with the measurement light 106 using a neighborhood of a cornea as a pivot point. The lenses 120-1 and 120-2 are configured such that each of the measurement light beams 106-1 through 106-3 is formed into an image at a given position on the retina 127.

An electric stage 117-2 can move in a direction indicated by an arrow and adjust and control the position of the associated lens 120-2. Each of the measurement light beams 106-1 through 106-3 is converged to a desired layer of the retina 127 by adjusting the position of the lens 120-2 so that an image thereof can be observed. In addition, the apparatus can deal with a case where the subject's eye 107 suffers from a refractive error. When the measurement light beams 106-1 through 106-3 are incident upon the subject's eye 107, the measurement light beams 106-1 through 106-3 are reflected or scattered from the retina 127. Thus, the measurement light beams 106-1 through 106-3 become return light beams 108-1 through 108-3 and return to the optical couplers 131-1 through 131-3, respectively. The electric stage 117-2 is controlled by the personal computer 125.

The present exemplary embodiment has a configuration in which the fiber ends 118-1 through 118-3 are arranged on the same plane (XY-plane). However, the configuration of the present exemplary embodiment is not limited thereto. The fiber ends 118-1 through 118-3 can be arranged in a direction (y-direction) perpendicular to a page plane of FIG. 1. Alternatively, positions of the fiber ends 118-1 through 118-3 can be arranged to have components in both directions perpendicular and parallel to the page plane. With the above configurations, the retina 127 can simultaneously be scanned with the three beams.

Next, a configuration of a detection system is described hereinafter. The return light beams 108-1 through 108-3 reflected or scattered by the retina 127 are combined with the reference light beams 105-1 through 105-3 by the optical couplers 131-1 through 131-3, respectively. Then, combined light beams 142-1 through 142-3 are incident upon the spectroscope. Thus, spectra are obtained by the line sensor 139. A tomographic image can be obtained by performing signal processing on the spectra with the personal computer 125.

The spectroscope is more specifically described hereinafter. With this configuration, a plurality of combined light beams are processed by the single line sensor. Accordingly, as compared with a case of using a two-dimensional sensor, the present exemplary embodiment can be carried out at low cost.

Figure 2:
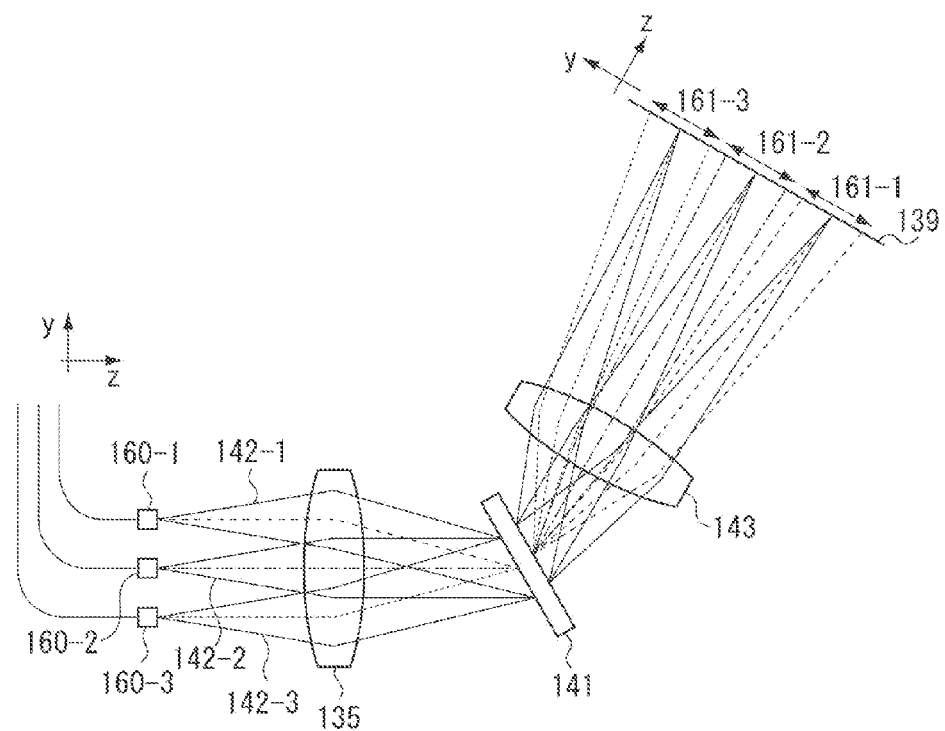
FIG. 2 illustrates a configuration of a spectroscope in the tomographic imaging apparatus.

FIG. 2 illustrates a configuration in which the three combined light beams 142-1 through 142-3 are incident upon the spectroscope, in order to describe the spectroscope illustrated in FIG. 1 in detail. Fiber ends 160-1 through 160-3 are arranged to be separated in the y-direction from one another. The combined light beams 142-1 through 142-3 are output from the fiber ends 160-1 through 160-3, respectively. At that time, the direction of each fiber end is preliminarily adjusted such that the combined light beams are output perpendicularly to a principal plane of the lens, in other words, the lens is telecentric. The "y-direction" is a direction parallel to a direction of dispersion by the transmission type diffraction grating 141 serving as a spectroscopic means. The output combined light beams 142-1 through 142-3 are incident upon the lens 135. The three combined light beams 142-1 through 142-3 are made by the lens 135 to be substantially parallel light beams. All the three combined light beams 142-1 through 142-3 are incident upon the transmission type diffraction grating 141.

In order to reduce a loss of an amount of light, it is necessary that the transmission type diffraction grating 141 is placed in vicinity of a pupil of an optical system, and that a stop is provided on a surface of the transmission type diffraction grating 141. Because the transmission type diffraction grating 141 is arranged to be inclined to the principal plane of the lens 135, a cross-section of a light flux on the surface of the transmission type diffraction grating 141 is oval. Accordingly, it is necessary to form the stop provided on the surface of the transmission type diffraction grating 141 into an oval shape.

The combined light beams 142 diffracted by the transmission type diffraction grating 141 are incident upon the lens 143. In FIG. 2, for simplicity of drawing, among light fluxes corresponding to the combined light beams 142-1 through 142-3, only a light flux corresponding to a central wavelength is illustrated, while only principal rays are illustrated corresponding to the other combined light beams. Because a z-direction is set as the direction of the optical axis, coordinates are rotated by the diffraction. Each of the combined light beams 142-1 through 142-3, which are diffracted and incident upon the lens 143, is formed into an image on the line sensor 139. Thus, interference fringes 161-1 through 161-3 are observed in the y-direction. More specifically, the spectroscope is configured such that images formed at positions of the fiber ends 160-1 through 160-3 are the interference fringes 161-1 through 161-3 formed on the line sensor 139.

Figure 3:
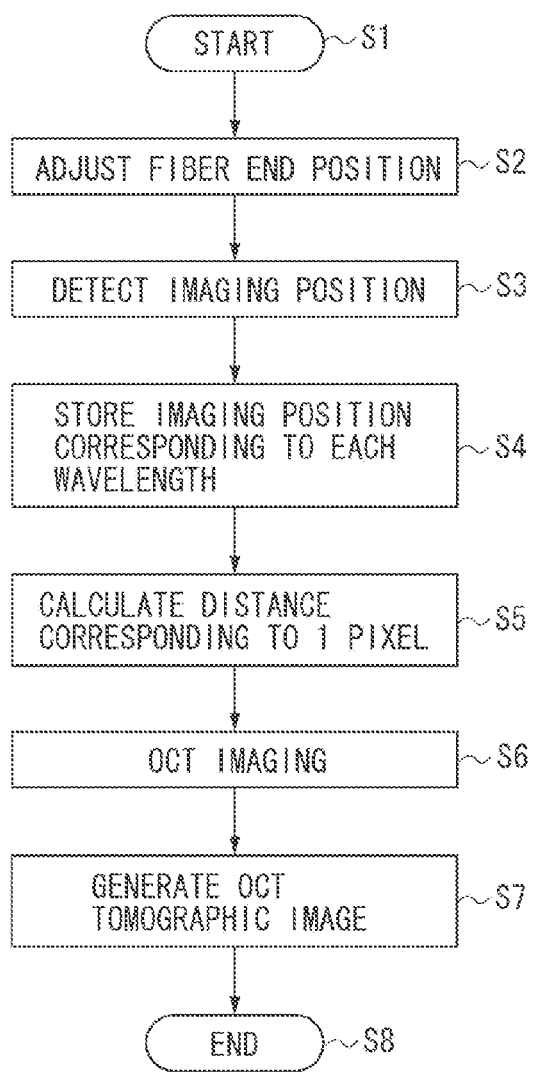
FIG. 3 illustrates a flow of a process of generating a tomographic image by the tomographic imaging apparatus.

FIG. 3 illustrates a process for adjustment/correction using the single-wavelength light source 102 according to the first exemplary embodiment and for generation of an OCT tomographic image.

In step S1, measurement is started. In this state, a tomographic imaging apparatus is activated.

In step S2, the positions of the fiber ends 160-1 through 160-3 are adjusted by outputting light beams of wavelengths of 815 nm and 865 nm.

As illustrated in FIG. 4A, a region on the line sensor 139 is acquired by splitting corresponding to the combined light beams 142-1 through 142-3. Then, tomographic images of the retina 127, which respectively correspond to the measurement light beams 106-1 through 106-3, can be obtained independent of one another by performing processing such as Fourier transform. If images are formed so that regions respectively corresponding thereto are separated from one another to the extent sufficient to prevent occurrence of crosstalk, as illustrated in FIG. 4A, no problem occurs. However, if images are formed closely to each other from the combined light beams 142-1 through 142-3, as illustrated in FIG. 4B, crosstalk occurs. Tomographic images of the retina 127 cannot be obtained corresponding to the measurement light beams independent of one another. In other words, one of the images overlaps with another of the images. Accordingly, it is necessary to separate the regions on the line sensor 139 from one another so as to prevent the images from overlapping with each other. However, if the regions are too far away separated from one another, pixels of the line sensor 139 are unnecessarily wasted. Thus, many pixels are needed. Accordingly, pixels of the line sensor 139 may become insufficient. Therefore, it is also necessary to make the regions as close as possible.

Because the wavelength width of the broadband light source 101 is not changed, a factor for determining whether crosstalk occurs is an interval between adjacent ones of the fiber ends 160-1 through 160-3. The interval between adjacent ones of the fiber ends 160-1 through 160-3 is adjusted such that images are formed from the combined light beams 142-1 through 142-3 at desired positions on the line sensor 139. Hereinafter, a procedure for adjusting the interval is described.

Figure 5A:
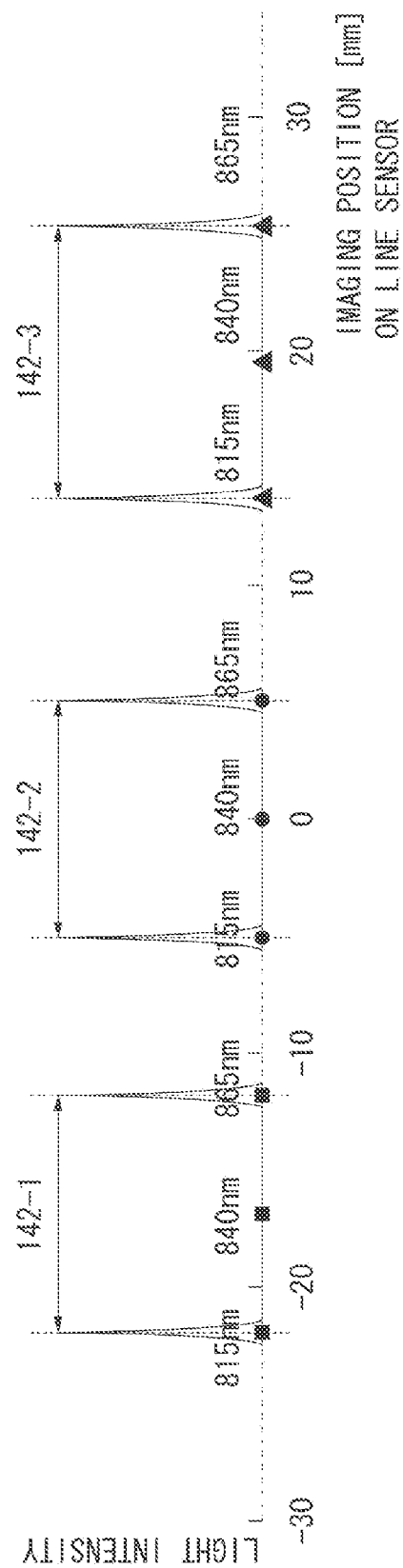
FIG. 5A conceptually illustrates outputs of the line sensor in the tomographic imaging apparatus at the time of making single-wavelength light incident thereon.

In FIG. 1, light having a wavelength of 815 nm and light having a wavelength of 865 nm pass through the optical couplers 155-1 through 155-3, the polarization controller 153-2, and the optical couplers 131-1 through 131-3 and are output from the fiber ends 160-1 through 160-3. Images are formed from the light having a wavelength of 815 nm, and light having a wavelength of 865 nm output from the fiber ends 160-1 through 160-3 at predetermined positions on the line sensor 139. In a state in which the interval between adjacent ones of the fiber ends 160-1 through 160-3 is not adjusted to an optimal value (i.e., a state illustrated in FIG. 4B, in which crosstalk occurs when light is irradiated from the broadband light source), the light having a wavelength of 815 nm, and the light having a wavelength of 865 nm form images at positions as illustrated in FIG. 5B. More specifically, the combined light beam 142-1 having a wavelength of 865 nm, the combined light beam 142-2 having a wavelength of 815 nm, the combined light beam 142-2 having a wavelength of 865 nm, and the combined light beam 142-3 having a wavelength 815 nm form images at positions where the adjacent ones are close to each other. In order to change this state to the desired state illustrated in FIG. 5A, the interval between the adjacent ones of the fiber ends 160-1 through 160-3 is adjusted while outputs of the line sensor 139 are checked. This adjustment can manually be performed. Alternatively, this adjustment can automatically be performed by an adjustment means (not shown) using a feedback loop while detection of an image-forming position is performed on the outputs of the line sensor 139 by a technique such as peak detection. Consequently, output positions, at which the combined light beams 142-1 through 142-3 are output, can be adjusted.

When the adjustment is manually performed, the state illustrated in FIGS. 5A and 5B is displayed on a screen of the personal computer 125. Then, the adjustment is performed by an operator while the operator watches the screen.

Figure 6:
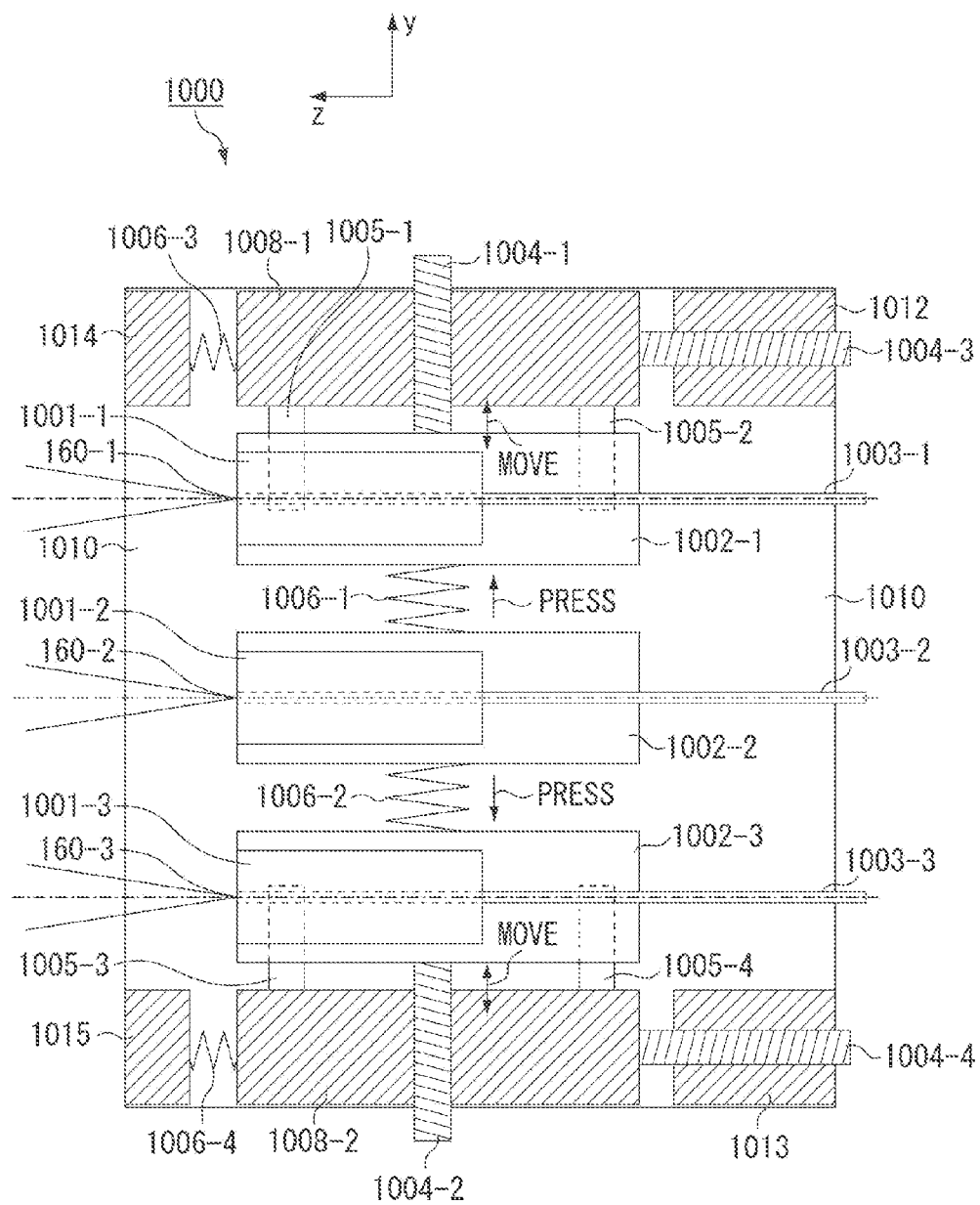
FIG. 6 schematically illustrates a configuration of a fiber end adjustment device in the tomographic imaging apparatus.

A fiber end adjustment device is described hereinafter with reference to FIG. 6. FIG. 6 illustrates a fiber unit portion and is taken from the y-direction illustrated in FIG. 2. In the fiber unit portion 1000, fiber portions 1000-1 through 1000-3 are connected to spectroscope-sides of the optical couplers 131-1 through 131-3. Each of the fiber portions 1003-1 through 1003-3 sandwiches fibers with a material such as quartz. The fiber portions are respectively fixed to holding portions 1001-1 through 1001-3, each of which has a polished side provided at the side of the fiber end portions 160-1 through 160-3. Each of the holding portions 1001-1 through 1001-3 is fixed to fiber base portions 1002-1 through 1002-3 by bonding. The central fiber base portion 1002-2 is fixed to a base 1010 with screws (not shown).

The base 1010 is adjusted with respect to an optical axis position (y) illustrated in FIG. 1, so that the central fiber end 118-2 is set at an optimal position where an optical axis of the apparatus is aligned and the lens 135 causes the combined light beams 142-1 through 142-3 to be parallel light beams. The upper fiber base portion 1002-1 and the lower fiber base portion 1002-3 illustrated in FIG. 6 are configured to perform relative movement with respect to the central fiber base portion 1002-2 in a direction (y-direction) of an interval between fibers. Taking the upper fiber base portion 1002-1 for example, the fiber base portion 1002-1 is provided with guide portions into each of which pins 1005-1 and 1005-2 fixed to a y-guide member 1008-1 are inserted. Thus, the fiber base portion 1002-1 is held movably in the y-direction.

In addition, a spring 1006-1 is provided between the fiber base portions 1002-1 and 1002-2. Consequently, the fiber base portion 1002-1 is pressed in the direction of an arrow (i.e., in a pressing direction) in the y-direction. A screw hole is provided in the y-guide member 1008-1. An adjustment screw 1004-1 is provided in the screw hole. In addition, the adjustment screw 1004-1 abuts on the fiber base portion 1002-1. Thus, the positioning of the fiber base portion 1002-1 in the y-direction is performed.

The interval between the fiber base portions 1002-1 and 1002-2 can be changed in the direction of the arrow (i.e., a moving direction) by rotation of the adjustment screw 1004-1. Thus, the interval between the fiber ends 160-1 and 160-2 can be adjusted. A similar configuration is provided at the side of the fiber base portion 1002-3. Consequently, the relative interval between adjacent ones of the combined light beams 142-1 through 142-3 can be adjusted. The relative interval is adjusted so that the apparatus is brought into a state in which no crosstalk occurs.

According to the present exemplary embodiment, as illustrated in FIG. 1, an incidence portion of the single-wavelength light source is configured by using an optical coupler in each reference light path to branch each reference light path in order to guide, to the spectroscope, reflection light or scattered light from an eye without a loss of an amount of light. However, as long as light of a single wavelength can be output from the fiber ends 160-1 through 160-3, the configuration of the incidence portion according to the present invention is not limited to a specific configuration. For example, if it is assumed that light output from a broadband light source and light of a single wavelength are used by switching, the apparatus can be configured by inserting a narrowband filter adapted to transmit only light of wavelengths of 815 nm and 865 nm into the broadband light source 101.

If in a measurement, a loss of an amount of light is ignorable, the apparatus can be configured to enable incidence of light of a single wavelength by branching one of a light path of the light source portion, a light path of the spectroscope, and a measurement light path using an optical coupler, similarly to the present exemplary embodiment, or by changing a light path using a mirror even in the air, or by branching the light path using a half mirror.

In the present exemplary embodiment, a method for adjusting the fiber ends, in which the broadband light source is turned off, has been described. However, light can simultaneously be irradiated from both of a single-wavelength light source and a broadband light source.

In step S3, light beams of wavelengths of 815 nm and 865 nm are output from the single-wavelength light source 102. Then, image-forming positions on the line sensor 139 are detected.

The present exemplary embodiment is configured such that combined light beams differ from one another in incidence angle to the diffraction grating 141, as illustrated in FIG. 2. Thus, the combined light beams differ in a diffraction angle from one another. Accordingly, the light beams having the same wavelength width differ from one another in the number of pixels detected by the line sensor 139. The relationship among the combined light beams, the incidence angles, the diffraction angles, the number of pixels, and the like is summarized in TABLE 1 described below. The line sensor 139 is assumed to have a pixel pitch of 12 μm.

TABLE 1

Relation between Combined Light and Imaging Position on Line Sensor

| Combined Light | Incidence Angle (°) | Wavelength λ | Diffraction Angle (°) | Image-forming Position [mm] | The Number of Pixels |
|---|---|---|---|---|---|
| 142-1 | 37.11 | 815.00 | 22.00 | −21.78 | 8.33 |
|  |  | 840.00 | 23.87 | −16.81 |  |
|  |  | 865.00 | 25.77 | −11.80 |  |
| 142-2 | 30.26 | 815.00 | 28.29 | −5.16 | 8.70 |
|  |  | 840.00 | 30.26 | 0.00 |  |
|  |  | 865.00 | 32.28 | 5.27 |  |
| 142-3 | 23.42 | 815.00 | 35.49 | 13.71 | 9.64 |
|  |  | 840.00 | 37.63 | 19.38 |  |
|  |  | 865.00 | 39.83 | 25.27 |  |

TABLE 1 describes the relationships among values calculated by assuming that the intervals between adjacent ones of the fiber ends 160-1 through 160-3 are 12 mm, and −12 mm, that a focal length of the lens 135 is 100 mm, that a focal length of the lens 143 is 150 mm, and that a pitch of the diffraction grating 141 is 1200 lines per mm. However, actually, images are not formed at the image-forming positions described in TABLE 1, because of error factors such as the arrangement of the diffraction grating 141, and the positions of the fiber ends 160-1 through 160-3. Accordingly, upon completion of adjustment of the positions of the above fiber ends 160-1 through 160-3, light from the single-wavelength light source 102 is incident upon the spectroscope again. Then, the number of pixels corresponding to the combined light beams 142-1 through 142-3 described in TABLE 1 is corrected.

A way of incidence of light from the single-wavelength light source 102 to the spectroscope has been described above. Image-forming positions respectively corresponding to wavelengths of 815 nm and 865 nm in the region, to which each of the combined light beams 142-1 through 142-3 is output, on the line sensor 139 are detected. The detection of the image-forming positions is performed by a detection method according to a technique such as peak detection, as described above.

In step S4, the positions of pixels on the line sensor 130, which are positions detected in step S3, are stored. The positions respectively corresponding to the two wavelengths associated with the three combined light beams are stored, so that a total of six pixel positions are stored. The positions of the pixels are stored by a memory or the like in the personal computer 125. Alternatively, another storage apparatus can be provided separately from the memory in the personal computer and store the positions of the pixels. A "used pixel number" is defined as a difference between a pixel position corresponding to the wavelength of 815 nm and that corresponding to the wavelength of 865 nm+1 pixel. The used pixel number corresponding to the combined light beam 142-1, that corresponding to the combined light beams 142-2, and that corresponding to the combined light beams 142-3 are designated with P1, P2, and P3, respectively.

According to the present embodiment, both end values of a used wavelength, which are 815 nm and 865 nm, are used as a value of the wavelength of light from the single-wavelength light source 102. However, light of an optional single wavelength can be incident upon the spectroscope. At that time, an image-forming position corresponding to the optical wavelength on the line sensor 139 can be known and higher precision correction can be performed.

In step S5, based on the six pixel positions stored in step S4, a converted distance per pixel (i.e., a corresponding physical distance to which a single pixel is converted) is calculated.

A physical resolution of a tomographic image is described hereinafter as a difference in optical characteristic in a depth direction of the inspection target due to the configuration of the optical system. Generally, this resolution is determined by a bandwidth of a light source. According to spectral domain optical coherence tomography (SD-OCT), if the maximum value and the minimum value of the number of pixels used for signal processing respectively agree with the maximum value and the minimum value of the wave number of a light source, the resolution SL is represented by the following expression (1).

$$\delta L = \frac{1}{2\Delta K} \quad \text{[Math. 1]}$$

In this expression, ΔK represents a wave number width. If the wavelength of light from the light source ranges from 815 nm to 865 nm, the wave number width=⅟₈₁₅ nm-⅟₈₆₅ nm. If the expression (1) is calculated by assuming a wavelength width as a difference between 815 nm and 865 nm, the resolution is 7 μm in the air. This value agrees with the value of a distance per pixel. For example, if the distance per pixel is 7 μm, a position at a distance of 1000 μm from a first pixel corresponds to a 142-th pixel. However, if the combined light beams differ from one another in the number of pixels of a corresponding image, it is inconvenient that images generated respectively corresponding to the three measurement light beams differ in the image size. Thus, the number of pixels of each smaller one of the images is increased to equalize the sizes of the images. It is convenient to set the number of the entire pixel-data of each image at $2^n$ by adding zero-pixels (i.e., performing zero-padding) to each image to perform fast Fourier transform. On the other hand, the numerical value of the bandwidth is increased, while the converted distance per pixel is reduced.

The number of pixels used in the image generated from the combined light beams 142-2 is P2. It is assumed that the number of pixels of the image having the equalized size is 1024. Thus, zero-pixels, the number of which is 1024-P2, are added to this image. At that time, the wavelength width obtained by setting the equalized size to be 1024 pixels is given and regarded as a bandwidth represented with the following expression (2) by assuming the central wavelength to be 840 nm and performing proportional calculation.

$$840 - \frac{1024 \times 25}{P_2} \le \text{wavelength} \le 840 + \frac{1024 \times 25}{P_2} \quad \text{[Math. 2]}$$

Then, the resolution $\delta L_2$ is calculated by substituting the converted distance per pixel (i.e., the corresponding physical distance to which a single pixel is converted) for the expression (1). The converted distance per pixel (i.e., the corresponding physical distance to which a single pixel is converted) is calculated by, e.g., setting the value P2=870 using the calculated value in TABLE 1. Thus, the converted distance per pixel obtained is 6.0 μm. Apparently, if the wavelength width corresponding to the number of the pixels used for the calculation is narrower than the bandwidth of the light source, a resolution corresponding to the converted distance per pixel is worse than the physical resolution.

$$\delta L_2 = \frac{1}{2\left(\frac{1}{840 - \frac{25600}{P_2}} - \frac{1}{840 + \frac{25600}{P_2}}\right)} \quad \text{[Math. 3]}$$

Similarly, the resolution corresponding to the combined light beam 142-1 is given by the following expression (4).

$$\delta L_1 = \frac{1}{2\left(\frac{1}{840 - \frac{25600}{P_1}} - \frac{1}{840 + \frac{25600}{P_1}}\right)} \quad \text{[Math. 4]}$$

The resolution corresponding to the combined light beam 142-3 is given by the following expression (5).

$$\delta L_3 = \frac{1}{2\left(\frac{1}{840 - \frac{25600}{P_3}} - \frac{1}{840 + \frac{25600}{P_3}}\right)} \quad \text{[Math. 5]}$$

The resolutions respectively corresponding to the combined light beams 142-1 and 142-3 are calculated by substituting the calculated values described in TABLE 1. Then, the resolutions $\delta L_1$ and $\delta L_3$ are obtained as follows: $\delta L_1 = 5.7$ μm; and $\delta L_3 = 6.6$ μm.

Thus, actual values of the converted distance per pixel are calculated according to the positions of the pixels stored in step S4 using the expressions (2) through (4).

In the calculation of the resolutions $\delta L_1$, $\delta L_2$ and $\delta L_3$, the proportional calculation is performed by assuming the central wavelength as 840 nm. However, if light of a given wavelength is output from the single-wavelength light source 102, it is useful to directly find a wavelength at which each of the numbers P1, P2, and P3 of the pixels is 1024.

In step S6, upon completion of storing data obtained by the above calculation, the irradiation with light from the single-length light source to the spectroscope is stopped. Then, ordinary OCT imaging is performed using the broadband light source.

Figure 7A:
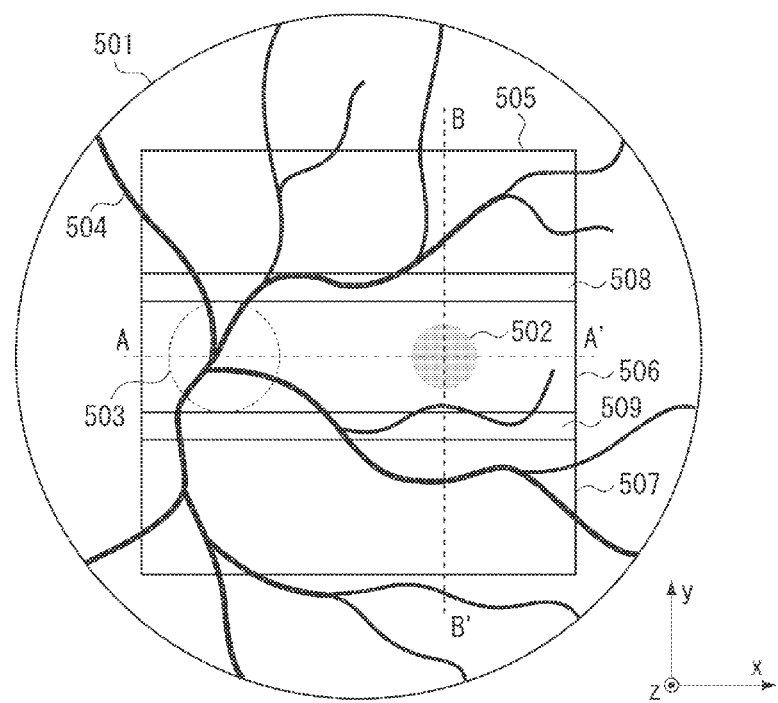
FIG. 7A illustrates a fundus imaged by the tomographic imaging apparatus.
Figure 7B:
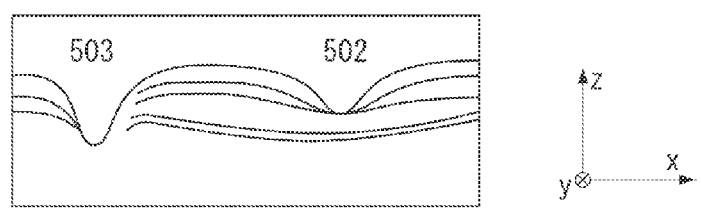
FIG. 7B illustrates a cross-section taken on line A-A' illustrated in FIG. 7A.
Figure 7C:
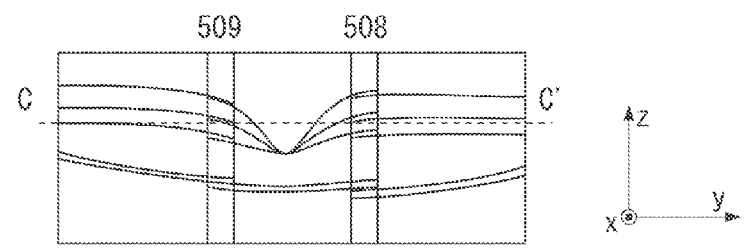
FIG. 7C illustrates a cross-section taken on line B-B' illustrated in FIG. 7A.

In step S7, a tomographic image is generated upon completion of making the numbers of pixels per line the same (e.g., 1024 in this case). It is sufficient for generating a tomographic image to perform generation processing, such as fixed noise removal, wavelength-wave-number conversion and Fourier transform, by imaging a general OCT tomographic image. FIG. 7B schematically illustrates a B-scan image of a cross-section taken on line A-A' illustrated in FIG. 7A. This B-scan image is obtained by single-wavelength measurement light. Thus, this B-scan image doesn't provide a feeling of strangeness. FIG. 7C schematically illustrates a B-scan image of a cross-section taken on line B-B' illustrated in FIG. 7A. More specifically, FIG. 7C illustrates an image obtained by combining B-scan images generated respectively corresponding to different combined light beams. The images of the cross-section become discontinuous due to the difference in resolution per pixel among the images. This is important for a C-scan image of a cross-section taken on line C-C'. Thus, a structure such as a blood vessel disappears or emerges in a boundary. A difference in contrast occurs due to a difference in a roll-off characteristic (i.e., a characteristic in which an OCT image becomes darker as a distance from a gate position increases), in addition to resolution.

In step S7, a tomographic image represented by a function $D_b(p, q, r)$ is obtained corresponding to each of the combined light beams. A functional argument "p" corresponds to a z-direction. Generally, the functional argument "p" is an element having 1024 integer values. However, due to symmetric properties coming from the Fourier transform, only 512 integer values (0-511) are extracted as the values of the functional argument "p". The functional argument "q" corresponds to the x-direction and has integer values (0-511). The functional argument "r" corresponds to a y-direction and has integer values (0-119). A parameter "b" corresponds to numbers of the combined light beams and has integer values (1-3).

A process of first obtaining spectra of 1024 pixels by interpolation of spectral data, and then performing Fourier transform may also be performed as a data enhancement process. Alternatively, it is advisable to perform the interpolation upon completion of generation of each tomographic image by setting the number of pixels per line to be the same as that stored in step S4.

More specifically, first, resampling in the z-direction is performed. This processing aims at equalizing the converted distances per pixel, which respectively correspond to the three measurement light beams. In this processing, a reference distance per pixel is assumed to be a converted distance corresponding to the second measurement light beam (i.e., the measurement light beam corresponding to the central measurement region). If linear interpolation is performed, the tomographic image is represented by the following expression (6) using the converted distance $L_b$ per pixel corresponding to each measurement light beam, and a floor function represented by what is called a Gauss symbol "[ ]". The converted distance $L_b$ per pixel is calculated in step S5 according to the numbers P1, P2, and P3 of used pixels. Generally, the function [x] represented using the Gauss symbol "[ ]" indicates a maximum integer that doesn't exceed "x". The tomographic image represented by the following expression (6) exhibits similar characteristics with respect to each of the variables "q" and "r". Thus, for simplicity of description, the function representing the tomographic image is expressed using only the variable "p" corresponding to the z-direction, without using the variables "q" and "r".

$$H_b(p) = \left(1 - \frac{pL_b}{L_2} + \left[\frac{pL_b}{L_2}\right]\right) D_b\left(\left[\frac{pL_b}{L_2}\right]\right) + \left(\frac{pL_b}{L_2} - \left[\frac{pL_b}{L_2}\right]\right) D_b\left(\left[\frac{pL_b}{L_2}\right] + 1\right) \quad \text{[Math. 6]}$$

In this expression, the function $H_b(p)$ represents a tomographic image after the interpolation is performed. As a result of the interpolation, the numbers of components of sets respectively corresponding to the measurement light beams differ from one another. However, it is sufficient to set the number of components at the minimum number of components among the sets respectively corresponding to the measurement light beams. In addition, the number of components can be set at a value smaller than the minimum number of components.

Next, normalization of depth-direction contrast in the z-direction is performed. More specifically, the roll-off characteristics respectively corresponding to all of the measurement light beams are preliminarily measured or simulated. The contrast is given by the following expression (7) by designating the roll-off characteristics with $R_b(p)$.

$$H_b(p,q,r)=D_b(p,q,r)/R_b(p) \quad \text{[Math. 7]}$$

However, the roll-off characteristics can be adjusted corresponding to the second measurement light beam.

$$H_b(p,q,r)=D_b(p,q,r)/R_b(p) \times R_2(p) \quad \text{[Math. 8]}$$

In step S8, the measurement is finished. When a 3D volume scan is performed, OCT measurement is performed while a scanner position is moved in the y-direction illustrated in FIGS. 7A through 7C. If there is another subject, the above steps are repeated.

Although it has been described that the imaging is performed subsequent to the adjustment processing, the apparatus can be configured such that the adjustment processing and the imaging are separately performed, and that the adjustment processing is performed, if necessary.

Thus, the adjustment of the positions of the fiber ends is performed using light of a single wavelength. The relationship between a wavelength width and a distance width on the line sensor is preliminarily corrected. Consequently, the apparatus can determine a correction value corresponding to each of images in a case of generating an OCT tomographic image of an inspection target using a plurality of measurement light beams. Thus, the apparatus can correct differences among the images. On the other hand, the relationship between a wavelength width and a pixel width on the line sensor is preliminarily obtained in an actual system. Consequently, the apparatus can determine a correction value corresponding to each of images in a case of generating an image of an inspection target using a plurality of measurement light beams. Thus, the apparatus can correct differences among the images.

According to the first exemplary embodiment, the apparatus is configured such that the fiber ends 160-1 through 160-3 are arranged in the y-direction, as illustrated in FIG. 2, and that three interference fringes observed in the y-direction are detected by the single line sensor. In contrast, according to a second exemplary embodiment, the apparatus is configured such that the fiber ends 160-1 through 160-3 are arranged in a direction (i.e., the x-direction) perpendicular to a page plane of FIG. 2, and that three interference fringes observed in the x-direction are detected by the sensor. The x-direction is perpendicular to a direction in which light is dispersed by the transmission type diffraction grating 141. The present exemplary embodiment is described hereinafter.

A configuration of a tomographic imaging apparatus according to the present exemplary embodiment is the same as that of the tomographic imaging apparatus according to the first exemplary embodiment. Accordingly, description of the configuration of a tomographic imaging apparatus according to the present exemplary embodiment is omitted.

Figure 8:
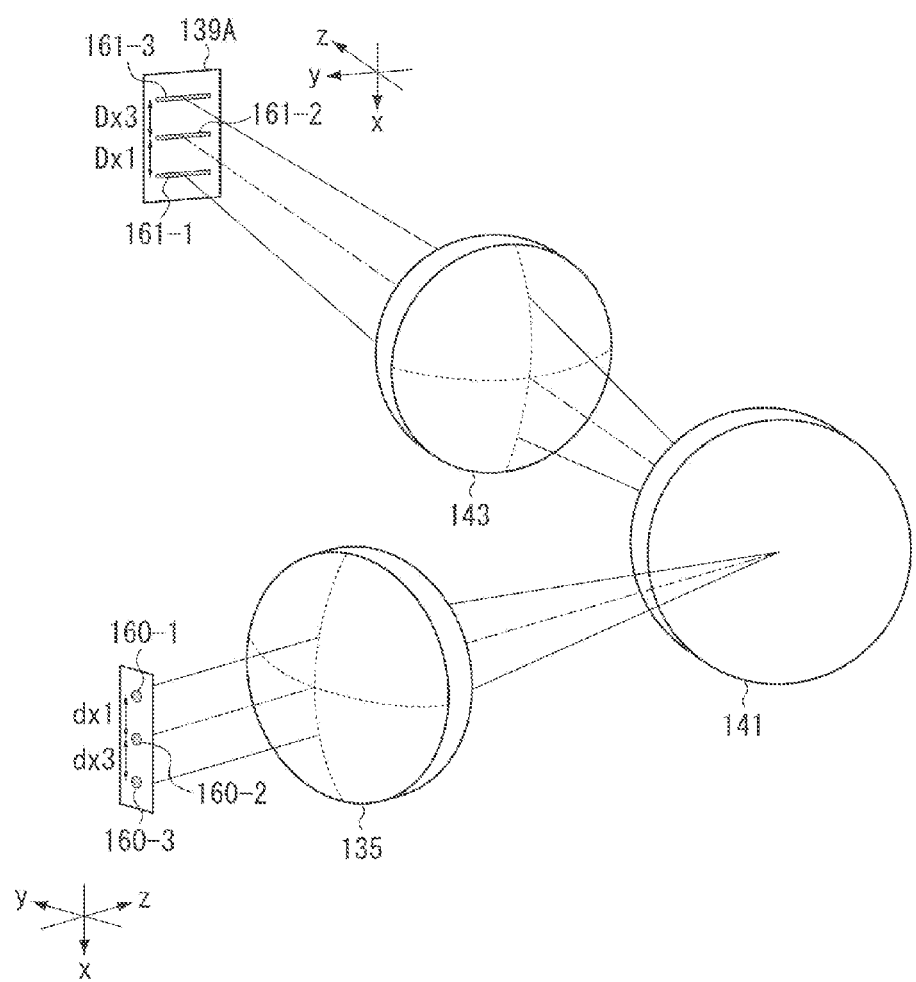
FIG. 8 illustrates a configuration of a spectroscope according to a second exemplary embodiment of the invention.

Hereinafter, a spectroscopic portion is more specifically described. FIG. 8 illustrates a configuration in which combined light beams 142-1 through 142-3 are incident upon the spectroscopic portion. In FIG. 8, for simplicity of drawing, only principal rays of a wavelength of 840 nm are illustrated. Combined light beams 142-1 through 142-3 are output from the fiber ends 160-1 through 160-3, respectively. Similar to the first exemplary embodiment, the second exemplary embodiment is such that directions of the fiber ends 160-1 through 160-3 are preliminarily adjusted so as to output the combined light beams 142-1 through 142-3 perpendicularly to a principal plane of a lens.

The combined light beams 142-1 through 142-3 are incident upon the lens 135. Then, the three combined light beams 142-1 through 142-3 are made by the lens 135 to be substantially parallel light beams. All of the three combined light beams 142-1 through 142-3 are incident upon the transmission type diffraction grating 141. Also similar to the first exemplary embodiment, according to the second exemplary embodiment, it is required to arrange the transmission type diffraction grating in vicinity of the pupil of the optical system, to provide a stop on the surface of transmission type diffraction grating 141, and to cross-sectionally form the stop into an oval shape.

The combined light beams diffracted by the transmission type diffraction grating 141 are incident upon the lens 143. Then, the combined light beams diffracted by the grating 141, which are incident upon the lens 143, form images on a line sensor array 139A, respectively, which are interference fringes 161-1 through 161-3. More specifically, the spectroscope is configured such that images at the fiber ends 160-1 through 160-3 become the interference fringes 161-1 through 161-3 formed on the line sensor array 139A. The line sensor array 139A is configured such that three line sensors are arranged in the x-direction. The interference fringes are formed on the three line sensors, respectively. However, the line sensor array 139A can be an area sensor.

In FIG. 8, intervals dx1 and dx3 are set at 1 mm and −1 mm, respectively. Similar to the first exemplary embodiment, the second embodiment is such that a focal length of the lens 135 is 100 mm, a focal length of the lens 143 is 150 mm, the pitch p of the transmission type diffraction grating 141 used therein is 1200 lines/mm, and a light source configured to output light having a central wavelength of 840 nm is used therein.

Figure 9A:
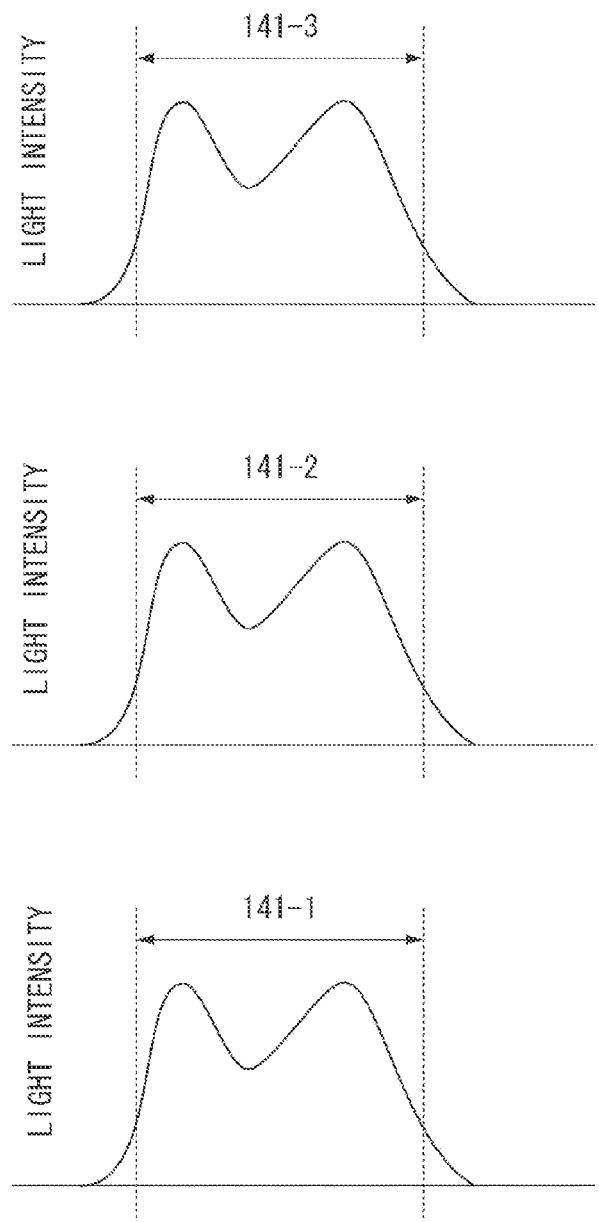
FIG. 9A conceptually illustrates spectroscopic positions on a line sensor according to the second exemplary embodiment of the present invention.
Figure 9B:
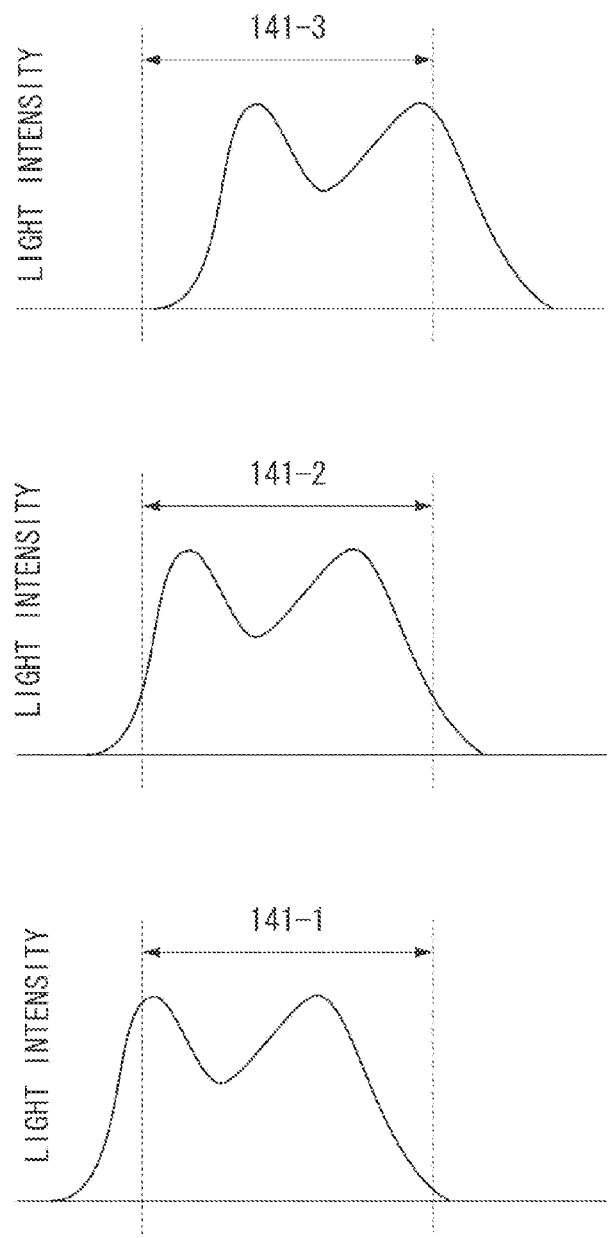
FIG. 9B conceptually illustrates spectroscopic positions on a line sensor according to the second exemplary embodiment of the present invention.

FIGS. 9A and 9B conceptually illustrate image-forming positions respectively corresponding to the combined light beams 141-1 through 141-3. FIG. 9A illustrates a state in which each of the combined light beams 141-1 through 141-3 forms an image at a desired position on a used pixel region indicated by an arrow. In this state, a domain of positions respectively corresponding to wavelengths of 815 nm through 865 nm of each of the combined light beams 141-1 through 141-3 substantially coincides with the used pixel region of 1024 pixels. On the other hand, FIG. 9B illustrates a state in which each of the combined light beams 141-1 through 141-3 doesn't form an image at a desired position on the used pixel region indicated by an arrow. In this state, the domain of positions respectively corresponding to wavelengths of 815 nm through 865 nm of each of the combined light beams 141-1 through 141-3 is shifted from the used pixel region of 1024 pixels.

An ordinary method of constructing an OCT image is to preliminarily determine what pixels are used, and to form an image by performing processing such as Fourier transform among the pixels to be used. However, sometimes, the combined light beams 141-1 through 141-3 are shifted from the pixels to be used, as illustrated in FIG. 9B. This situation occurs when the fiber ends 160-1 and 160-3 are deviated in the y-direction from the fiber end 160-2. When an OCT image is constructed in a state in which the used pixel region is shifted from the positions at which images are formed from the combined light beams, the processing is performed on a zone shifted from the domain of the positions respectively corresponding to wavelengths of 815 nm through 865 nm. This results in occurrence of problems that the position in the z-direction of an OCT image differs from an actual position thereof, and that an amount of light is wasted.

In order to solve the problems, light of a single wavelength is incident upon the spectroscope. Basically, in steps similar to those according to the first exemplary embodiment, a process from the detection of the image-forming position to the generation of an OCT tomographic image is performed. FIG. 10 conceptually illustrates an output of the line sensor array 139A at the time of making light from a single-wavelength light source incident upon the spectroscope. Based on this output, the image is corrected.

Next, imaging according to the second exemplary embodiment is described hereinafter with reference to a flowchart illustrated in FIG. 2. In step S1, measurement is started. Step 2 is not performed according to the second exemplary embodiment. In step S3, the image-forming position corresponding to each wavelength is detected, as illustrated in FIG. 10. In step S4, the image-forming position detected in step S3 is stored in the personal computer 125.

In step S5, the converted distance per pixel is calculated from the image-forming position stored in step S4 using the expressions (2) to (4). In step S6, OCT imaging is performed.

In step S7, an OCT tomographic image is generated while the image is corrected using the expressions (5) and (6). In step S8, the measurement is finished.

If the fiber ends 160-1 through 160-3 are arranged in the x-direction, similarly to the present exemplary embodiment, the fiber ends 160-1 through 160-3 show substantially the same relationship between the wavelength width and the used pixel width. Thus, the fiber ends can be adjusted such that images corresponding to the combined light beams 141-1 through 141-3 are formed on the used pixel region that is predetermined. At that time, in step S2, the intervals of the fiber ends 160-1 through 160-3 are adjusted while outputs of the line sensor array 139A are observed. Because the fiber ends 160-1 through 160-3 show substantially the same relationship between the wavelength width and the used pixel width, steps S3 through S5 can be omitted. In step S6, OCT imaging is performed. In step S7, the ordinary generation of an OCT image is performed.

The apparatus according to the present exemplary embodiment is configured such that three combined light beams are incident upon the spectroscope. However, the configuration of the apparatus according to the present exemplary embodiment is not limited thereto. Even a configuration in which only one combined light beam is incident thereon is useful. Even in this configuration, similar to the above process according to the present exemplary embodiment, a process is performed, which includes steps of causing light of a single wavelength to be incident, detecting image-forming positions, determining used pixels, performing OCT imaging, and generating an OCT tomographic imaging.

Thus, an OCT image can be generated without wasting an amount of light, or making the position in the z-direction of an OCT image different from an actual one.

A third exemplary embodiment is the same as the first exemplary embodiment in the configuration of the optical system and in that of the spectroscope.

The third exemplary embodiment differs from the first exemplary embodiment in that the adjustment of the positions of the fiber ends for adjusting an amount of crosstalk is omitted in step S2. According to the third exemplary embodiment, the adjustment of the positions of the fiber ends is once performed. Then, step S2 is omitted in the subsequent measurement by fixing the adjusted positions of the fiber ends. At that time, after starting step S1, a process proceeds to step S3 in which the image-forming position corresponding to each wavelength is detected. More specifically, a process of generating a tomographic image according to the present exemplary embodiment includes the following steps.

In step S1, measurement is started. Then, in step S3, image-forming positions corresponding to each wavelength as illustrated in FIGS. 5A and 5B are detected. In step S4, the image-forming positions detected in step S3 are stored in a memory or the like of the personal computer 125.

In step S5, a converted distance per pixel is calculated from the image-forming positions stored in step S4 using the expressions (2) through (4). In step S6, OCT imaging is performed.

In step S7, an OCT tomographic image is generated while the image is corrected. In step S8, the measurement is finished.

Thus, the relationship between the wavelength width and the distance width on the line sensor is preliminarily corrected using light of a single wavelength. Consequently, a correction value corresponding to each image in the case of generating an OCT tomographic image of an inspection target using a plurality of measurement light beams is determined. Accordingly, differences among images can be corrected.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-082813 filed Mar. 31, 2010, which is hereby incorporated by reference herein in its entirety.

The invention claimed is:

1. A tomographic imaging apparatus comprising:
   an irradiation unit configured to irradiate with a plurality of measurement light beams;
   a sensor configured to convert into an electric signal a plurality of combined light beams via an optical imaging system by making return light beams from an inspection target, which are generated due to the plurality of measurement light beams, interfere with reference light beams;
   an output unit configured to output light beams of a single wavelength based on a wavelength width of the plurality of measurement light beams;
     an adjustment unit configured to adjust output positions of the combined light beams, based on the positions of the light beams of the single wavelength on the sensor; and
   a generation unit configured to generate a tomographic image from an electric signal acquired by the sensor via the imaging optical system, based on a position of the light beam of the single wavelength on the sensor.

2. The tomographic imaging apparatus according to claim 1,
   wherein the output unit outputs light beams of two or more wavelengths.

3. The tomographic imaging apparatus according to claim 1, wherein a light beam of the single wavelength output from the output unit is incident upon a reference light path through which the reference light beam is transmitted or reflected.

4. The tomographic imaging apparatus according to claim 1, wherein the output unit includes a broadband light source and an optical filter, and wherein the optical filter transmits or reflects a light beam of a specific wavelength.

5. The tomographic imaging apparatus according to claim 1, wherein the number of measurement light beams and that of combined light beams are plural.

6. The tomographic imaging apparatus according to claim 5, wherein the imaging optical system includes a spectroscopic unit having diffraction angles in which the plurality of light beams differ from one another, and wherein the generation unit generates the tomographic image by correcting, based on positions of light beams of the single wavelength on the sensor, a difference in optical characteristic, which is included in the combined light beams generated at the different diffraction angles, in a direction of depth of the inspection target.

7. A tomographic imaging method for imaging a tomographic image using combined light obtained via an optical imaging system with a sensor to make return light caused by irradiation of measurement light onto an inspection target and reference light, interfere with each other, the tomographic imaging method comprising:

outputting light beams of a single wavelength, based on a wavelength width of the measurement light; and generating a tomographic image from an electric signal acquired by the sensor, based on a position of the light beam of the single wavelength on the sensor via an optical imaging system.

* * * * *